(12) United States Patent
Pierson et al.

(10) Patent No.: US 11,938,240 B2
(45) Date of Patent: Mar. 26, 2024

(54) METHOD AND APPARATUS FOR PLANNING A DISINFECTION PATH FOR AN AUTONOMOUS, MOBILE ROBOTIC DEVICE

(71) Applicant: AVA ROBOTICS INC., Cambridge, MA (US)

(72) Inventors: Alyssa Pierson, Somerville, MA (US); Saman Amarasinghe, Weston, MA (US); Daniela Rus, Weston, MA (US); Marcio Macedo, Cambridge, MA (US); Youssef Saleh, Arlington, MA (US)

(73) Assignee: AVA ROBOTICS INC., Cambridge, MA (US)

( * ) Notice: Subject to any disclaimer, the term of this patent is extended or adjusted under 35 U.S.C. 154(b) by 168 days.

(21) Appl. No.: 17/520,651

(22) Filed: Nov. 6, 2021

(65) Prior Publication Data
US 2022/0143237 A1    May 12, 2022

Related U.S. Application Data

(60) Provisional application No. 63/110,784, filed on Nov. 6, 2020.

(51) Int. Cl.
*A61L 2/10*    (2006.01)
*A61L 2/24*    (2006.01)
(Continued)

(52) U.S. Cl.
CPC .................. *A61L 2/10* (2013.01); *A61L 2/24* (2013.01); *B25J 15/0019* (2013.01); *G01C 21/343* (2013.01); *G01C 21/383* (2020.08); *G05D 1/0094* (2013.01); *G05D 1/0219* (2013.01); *G05D 1/0223* (2013.01); *G05D 1/0274* (2013.01); *A61L 2202/11* (2013.01);
(Continued)

(58) Field of Classification Search
CPC .......... A61L 2/10; A61L 2/24; A61L 2202/11; A61L 2202/14; A61L 2202/16; A61L 2202/25; A61L 2209/111; A61L 9/20; B25J 15/0019; B25J 5/007; B25J 11/008; G01C 21/343; G01C 21/383; G01C 21/005; G01C 21/206; G05D 1/0094; G05D 1/0219; G05D 1/0223; G05D 1/0274; G05D 2201/0203
See application file for complete search history.

(56) References Cited

U.S. PATENT DOCUMENTS

| 11,348,269 | B1 * | 5/2022 | Ebrahimi Afrouzi ... G01S 17/48 |
| 2021/0299295 | A1 * | 9/2021 | Rubaek .................... A61L 2/24 |
| 2021/0347048 | A1 * | 11/2021 | Trevor .................. G05D 1/0214 |

* cited by examiner

*Primary Examiner* — Anne Marie Antonucci
*Assistant Examiner* — Jewel Ashley Kuntz
(74) *Attorney, Agent, or Firm* — Caldwell Intellectual Property Law

(57) ABSTRACT

An autonomous, mobile robotic device (AMR) is configured with one or more UVC radiation sources, and operates to traverse a path while disinfecting an interior space. Each UVC radiation source is connected to the AMR by an articulating arm that is controlled to orient each source towards a feature or surface that is selected for disinfection during the time that the AMR is moving through the space. The location of each feature selected for disinfection can be mapped, and this map information, a current AMR location and pose can be used to generate signals that are used to control the articulating arm to orient each UVC lamp towards a feature that is selected for disinfection.

18 Claims, 7 Drawing Sheets

(51) Int. Cl.
*B25J 5/00* (2006.01)
*B25J 15/00* (2006.01)
*G01C 21/00* (2006.01)
*G01C 21/34* (2006.01)
*G05D 1/00* (2006.01)
*G05D 1/02* (2020.01)

(52) U.S. Cl.
CPC ....... *A61L 2202/14* (2013.01); *A61L 2202/16* (2013.01); *B25J 5/007* (2013.01); *G05D 2201/0203* (2013.01)

FIG. 6

SPEED/LAMP LOOKUP TABLE 345D

| CALC. DOSE/WEIGHT VALUE | SPEED | LAMP ON/OFF |
|---|---|---|
| WEIGHT = A | .5 m/sec. | ON |
| WEIGHT = B | .7m/sec. | ON |
| WEIGHT = C | 1.0m/sec. | OFF |

METHOD AND APPARATUS FOR PLANNING A DISINFECTION PATH FOR AN AUTONOMOUS, MOBILE ROBOTIC DEVICE

1. FIELD OF THE INVENTION

The present disclosure relates to disinfecting an environment using a UVC radiation source attached to a mobile, autonomous robotic device.

2. BACKGROUND

Autonomous, mobile robotic devices (AMRs) can be designed for use in a variety of different environments for a variety of different applications. Some AMRs are designed for distribution center applications, others are designed to clean interior surfaces, still others are designed to support interaction with humans in a hospital setting or for audio and/or video communication applications. Still other AMRs have been designed for security applications, and some have been designed to rid interior areas occupied by humans of dangerous pathogens, such as bacteria and viruses.

Generally, AMRs designed for the applications mentioned above can have functionality that enables them to autonomously follow a predetermined path through their environment, and they can be designed to have a variety of different types of sensors that enable them to determine where they are located in their environment, avoid obstructions in their path, to determine how far and in what direction they travel, and they can have functionality that permits them to wireless communicate audio, video or data over a network with an AMR user.

With the advent of viral pandemics, the disinfection of interior spaces has become an important human health issue. In this regard, there are a number of different disinfection methods being used to rid spaces of harmful pathogens. For example, disinfecting liquids or aerosol sprays can be applied to a surface. Other effective means for disinfecting surfaces are the use of a filtration or ozonation device, and light sources of particular wavelengths are also an effective means for disabling many pathogens. Specifically, electromagnetic radiation having a wavelength in the 110-280 nm range (i.e., ultraviolet C radiation/light or UV-C light) is being used to effectively disinfect surfaces harboring pathogens that are dangerous to human health. In this regard, hand-held UV-C light sources are available that allow a user to direct the light source towards an area to be disinfected while moving around a space. Carts having UV-C light sources are available that can be manually pushed around to disinfect a space. More recently, autonomous, mobile robotic devices having attached UV-C light sources have become available that can be controlled disinfect interior spaces.

4. BRIEF DESCRIPTION OF THE DRAWINGS

FIG. 6 is a block diagram showing a lookup table 345D.

5. DETAILED DESCRIPTION

Figure 1A:
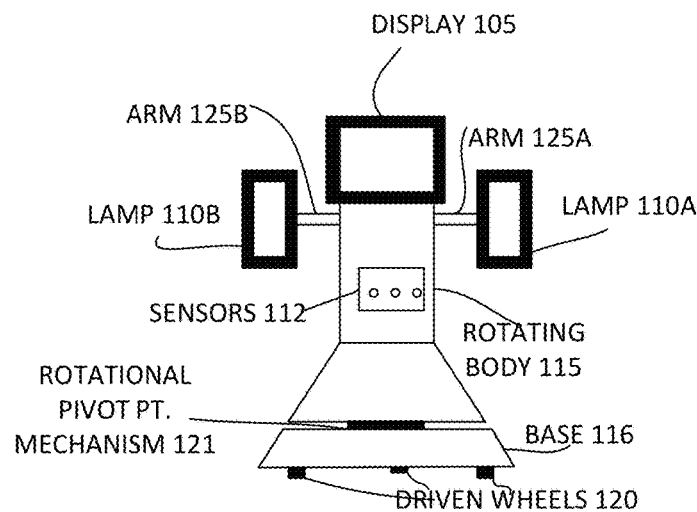
FIG. 1A is a diagram showing elements comprising a disinfecting, autonomous, mobile robotic (D-AMR) device 100.

Generally, autonomous, mobile robotic devices capable of disinfecting an area in an interior space using UV-C (UVC) radiation are configured with UVC light or radiation sources which are fixedly mounted to the AMR in such a manner so as to disinfect an area within a 360-degree radius around the AMR, and at various distances (depending upon the power of the light) from the AMR. This sort of configuration can be dangerous to humans, and other living things sharing the area being disinfected, as exposure to UVC radiation for any period of time can be dangerous, and can lead to skin cancer or eye cataracts. As not all surfaces or features in an interior space need disinfection, and since a disinfecting capable AMR, hereinafter referred to as a D-AMR, relies upon battery power for operation, a D-AMR configuration having continuous 360-degree disinfection can waste energy and limit battery life.

D-AMRs can be provided with a map generated by a user, or they can automatically generate a map, that identifies features/surfaces in an area to be disinfected, and the D-AMR can follow a predetermined path through the mapped space at a constant rate of speed with the UVC light turned on constantly until it reaches the end of the path. Provided that a D-AMR typically traverses a path at a constant rate of speed, and in order to adequately disinfect all of the surfaces in a given space, it is necessary to control the rate of speed at which the robot traverses a path to be relatively slow. This slow rate of speed can be an unnecessary drain on a battery, and/or require the D-AMR to have a larger, more expensive battery. Further, a D-AMR user must assume that a space, after being traversed by the D-AMR, has been adequately disinfected based upon the rate of speed of the device, the path of the device, the UVC source intensity and configuration on the AMR. However, such an assumption that the space has been adequately disinfected can be erroneous. Further, in the event that objects in the space have been moved since a disinfection path was determined, these objects can cast what amounts to a disinfection shadow, resulting in some surfaces not being disinfected.

Accordingly, we have designed a D-AMR device configured to have one or more UVC radiation or light sources attached to it which operates to disinfect selected features and surfaces in an interior area, such as a meeting room, cafeteria, or any area that is commonly occupied by humans or other living things. This D-AMR traverses a path through an area that is planned based upon a disinfection need of selected features and surfaces in the area. These features can be selected by a user of the D-AMR, or they can be autonomously selected by functionality operating under the control of the D-AMR.

According to one embodiment, the speed or speeds at which the D-AMR moves along at least some portions of a path to disinfect an interior area can depend upon a configuration of UVC light sources (i.e., number, type, intensity, and/or orientation of UVC light sources) attached to the D-AMR. Given a particular UVC light source configuration, it is possible to calculate a disinfection dosage model needed to be applied to different features or surfaces in an area and a disinfection dosage estimate actually applied to an area in order to substantially neutralize or kill harmful pathogens living on the features or surfaces. This dosage information can be utilized by the D-AMR to determine a speed and whether the UVC lights are turned on or off at different points along the disinfection path. Further, the path followed by the D-AMR through the area to be disinfected is determined by the features to be disinfected, and by the disinfection need (i.e., dosage) of each feature. As described herein, a disinfection dosage can be measured by an amount of UVC radiation applied to and received by a selected feature over some period of time.

According to another embodiment, the D-AMR is comprised of a robot body, drive and sensor systems, and one or more UVC light sources attached to the robot body. Depending upon the location of the D-AMR along the disinfection path, the location of features selected for disinfection, and based upon the desired disinfection dosage that needs to be applied at particular locations, the orientation of some or all of UVC light sources comprising a D-AMR can be controlled independently with respect to an orientation of the robot body in order to direct UVC radiation towards the features selected for disinfection. Further, one or all of the UVC light sources can have reflectors attached to them so that the radiation emitted by the light sources is directed towards the features selected for disinfection, and so that the radiation is directed away from living objects that it can harm (i.e., humans, plants, and animals).

According to another embodiment, as the D-AMR traverses a path through an area, it gathers information that can be used to generate a 2-D or 3-D heat map that visually illustrates a total amount of UVC radiation that has been applied over time to different features comprising the area.

Figure 1B:
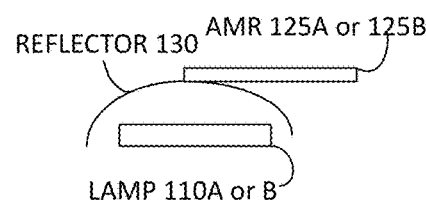
FIG. 1B is a diagram showing elements comprising a UVC lamp 110a or 110b.

The aforementioned embodiments will now be described with reference to the figures, in which FIG. 1A is an illustration of physical features comprising a D-AMR 100 having two UVC light sources (hereinafter referred to as UVC lamps) 110a and 110b. Each of the UVC lamps can have a reflector 130, shown with reference to FIG. 1B, that functions to direct the UVC radiation towards features in an interior area that have been selected for disinfection. The D-AMR 100 has a robot body 115 able to be rotated around a pivot point 121 with respect to a base 116, and the base 116 has a number of driven wheels 120 that can be controlled by a drive system to move the D-AMR around an interior area. The D-AMR can also have a display 105 and can have one or more sensors 112 that can be employed to, among other things, generate a map of the space through which the D-AMR is traversing, and to capture images of objects in the area. Generally, according to one embodiment, the D-AMR can operate autonomously to generate maps and locate features in an interior area, and to perform path-planning in the interior area. The D-AMR can be controlled to move at speeds of between 0.1-1.0 meters per second. As will be described later in more detail with reference to FIG. 3, a mapping module can have laser range scanning (Lidar) and simultaneous localization and mapping functionality (SLAM) that the D-AMR can employ to map and localize objects in an area and to generate a visual representation of the map. During operation, the D-AMR can localize its position within a mapped area using both the lidar functionality and internal odometry. The D-AMR can also be configured to have one or more depth cameras used for capturing image information used to identify different types of objects, and used for dynamic obstacle avoidance and collision detection. Also, a charging station (not shown) can be provided that the D-AMR can move to in order to automatically charge on-board batteries without human intervention. Configured in such a manner, the D-AMR is able to, independently of human control, map an area, identify features in the area that can be disinfected, plan an optimal path through the area and traverse the path while controlling the orientation of UVC lamps to disinfect the identified features.

Further, and as described later, the D-AMR 100 can operate to create a model to accurately predict a disinfection dosage a surface in a area will receive from the D-AMR. The dosage information can be used to control a speed of the D-AMR and to control the operation of the UVC lamps during the time it traverses a path through the area. Also, the D-AMR can operate to verify a dosage received by a surface during the time it traverse a path by collecting odometry and sensor information. This information collected by the D-AMR can be used to create a visual heat-map that provides a user with verification that an area has been disinfected.

According to the embodiment shown with reference to FIG. 1A, the UVC lamps 110a and 110b are shown to be connected to the robot body by arms 125a and 125b respectively, and each arm can be controlled to rotate the UVC lamps around an axis that runs along the length of the arm to cause the UVC radiation to be directed at different angles with respect to a horizontal plan of a floor surface 130 in the interior area on which the D-AMR can move. Rotating the UVC lamps in this manner permits the D-AMR to control the UVC radiation to be directed to features in the space that are positioned to be higher or lower with respect to the floor 130. For example, if a feature to be disinfected is chair having a surface that is twenty inches above the floor, then the UVC lamps can be rotated upward or downward as appropriate so that more UVC radiation is directed towards the chair, or the feature to be disinfected is a table surface that is thirty inches above the floor level, then the UVC lamps can be rotated as appropriate so that more of the UVC radiation is directed towards the table surface. The ability to control the orientation of the UVC lamps allows the D-AMR to more effectively and efficiently disinfect selected features (maybe faster or more efficiently) as it moves through the interior space. According to another embodiment, the arms 125A and 125B are not able to be rotated, and have no degrees of movement freedom. Alternatively, the UVC lamps have reflectors and can be fixedly mounted to an arm so that rotation with respect to the arm is not possible. According to this embodiment, the direction in which the UVC radiation is emitted is controlled by the orientation of the D-AMR.

Figure 2:
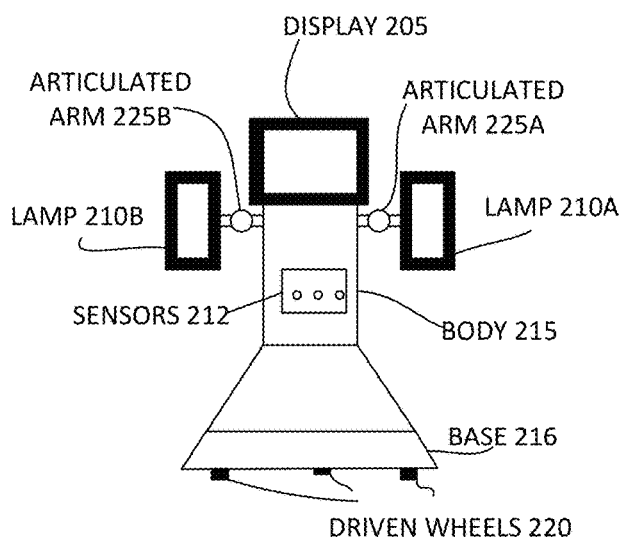
FIG. 2 is a diagram showing elements comprising a D-AMR device 200.

According to another embodiment of the D-AMR 100 in FIG. 1A, a D-Amr 200 shown with reference to FIG. 2 has UVC lamps 210a and 210b that can be connected to the robot body by respective articulated robotic arms 225a and 225b, each of which can have multiple degrees of movement freedom. These articulated arms can be controlled to orient the lamps so that the UVC radiation is directed towards selected features in the area being disinfected by the D-AMR. Further, one or both of the articulated arms can have a telescopic capability so that the UVC lamps can be extended towards a feature to be disinfected. Such an articulated arm permits the D-AMR to more effectively disinfect features in an area.

Figure 3:
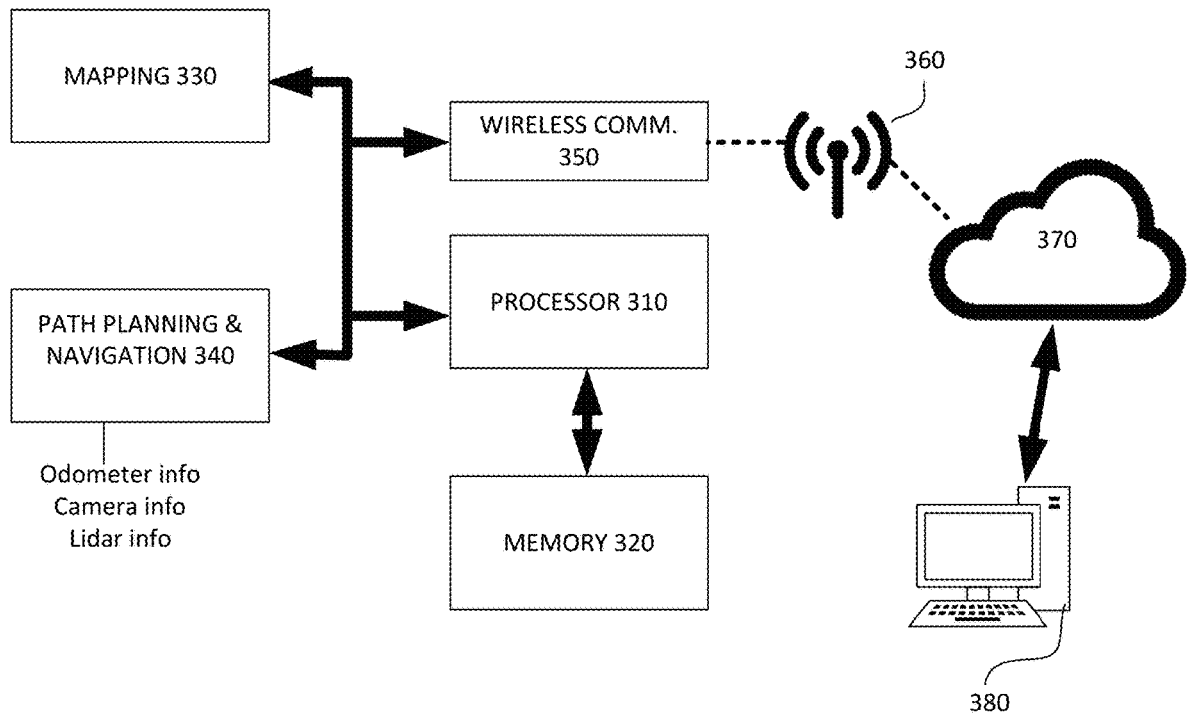
FIG. 3 is a block diagram illustrating functional elements comprising either of the D-AMR devices 100 or 200.

Referring now to FIG. 3, which is a diagram illustrating functional elements comprising either of the D-AMRs 100 or 200, and which are collectively referred to here as functional modules 300. A processor 310 is in communication with a non-transitory, computer memory device (memory) 320 that maintains information generated by any of the functional modules 300, and which maintains information that can be used by the processor to control the operation of the D-AMRs. More specifically, the processor 310 can operate to control functionality associated with each of the modules 300 to generate and store information used by the D-AMR to disinfect particular features in an interior area. The location of the memory 320 with respect to the D-AMR is not important to the operation of the D-AMR. The memory device 320 can be on-board the D-AMR as shown in FIG. 3, or it can be located remotely to the D-AMR in a device comprising the network 370 or on the user device 380. A mapping function 330 generally operates to receive information from different types of sensor devices, and to use this information to create either 2-D or 3-D maps of the space in which the D-AMR is operating, and to identify and locate particular features and surfaces that can be designated for disinfection in an area. A path-planning and navigation function 340 generally operates on information generated by the mapping function 330 to determine an optimal path for the D-AMR to traverse through the area while performing disinfection, to calculate dosages of UVC radiation to be applied to features located at different points along the path, and to determine a particular rate of speed at which the D-AMR can move along particular portions of the path while disinfecting the identified features. The module 340 also has functionality that can operate to control the state of each UVC lamp to be on or off, and to control the movement of each articulated arm in order to orient the lamps to be pointing towards a feature identified for disinfection. The D-AMR also has a wireless communication adapter 350 that operates to receive signals from and send signals to a wireless access point 360 which operates in conjunction with a network 370 to route signals to and from the D-AMR. Finally, a D-AMR user can operate a computational device 380 (i.e., PC or server) that is connected to the network 360 that can be used to control or monitor certain aspects of the D-AMR operation.

Figure 4:
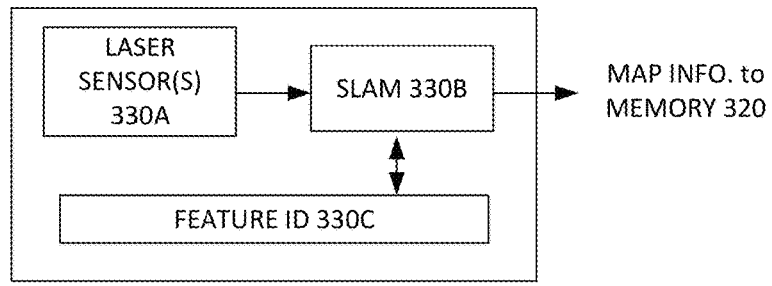
FIG. 4 is a block diagram illustrating functional elements comprising a mapping module 330.

Turning now to FIG. 4, which shows the mapping functionality 330 having laser sensing functionality 330A, SLAM functionality 330B, and feature identification functionality 330C. The laser sensor functionality can be implemented in a 2-D or 3-D light detection and ranging (Lidar) device, for example, and the output from this sort of sensor is typically 2-D (x,y) or 3-D (x,y,z) point cloud information. Information collected from one or more laser sensing devices 330A can be used by a SLAM (Simultaneous Location and Mapping) algorithm to construct a visual map showing the various features comprising an area, such as walls, floors, tables, chairs, counters, etc. The identify and position of at least some features comprising the area can be determined by the feature ID functionality 330C, which can be implemented in a neural network that is trained to identify features that a user is interested in disinfecting, such as floors, walls, tables, chairs, counters, etc. The output of the mapping function 330 can be sent to the memory 320 where it is stored, and this output is comprised of a map of the area showing, among other things, the location and identity of features identified by the feature ID functionality 330C. It should be understood that while the mapping functionality 330 is described as being implemented using a Lidar device, this mapping function can also be implemented using an image acquired from cameras or other image sensing devices as opposed to a Lidar device.

The path planning and navigation (PPN) module 340 will now be described with reference to FIG. 5. The PPN module 340 has path planning functionality 341 and a D-AMR navigation functionality 345. The path planning functionality 341 generally operates under control of the processor 310 to generate a graph structure by selecting locations for a plurality of nodes in a mapped area, identifying all possible paths between the nodes, wherein a path between any two nodes indicates the existence of an edge, calculating and assigning a weight to each edge, and determining an optimum path through the graph. According to one embodiment, a graph generation function 342 can be controlled to select node locations independent of any user input, or according to another embodiment the nodes can be manually selected by a user. Regardless of whether the position of a node is selected by the function 342 or a user, the position of each node is selected such they can provide a sufficient dose of disinfection to all features and surfaces of interest in an area. These nodes are not necessarily evenly spaced, but can be spaced at a distance such that if a robot visits a node, it will provide a sufficient disinfection dosage to the environment surrounding that node. For example, if a room contains four nodes, by visiting all four nodes, the robot can provide a sufficient dosage to the entire room. Nodes are also placed as navigation waypoints between regions of disinfection, such as navigating down a corridor to an area.

Figure 7:
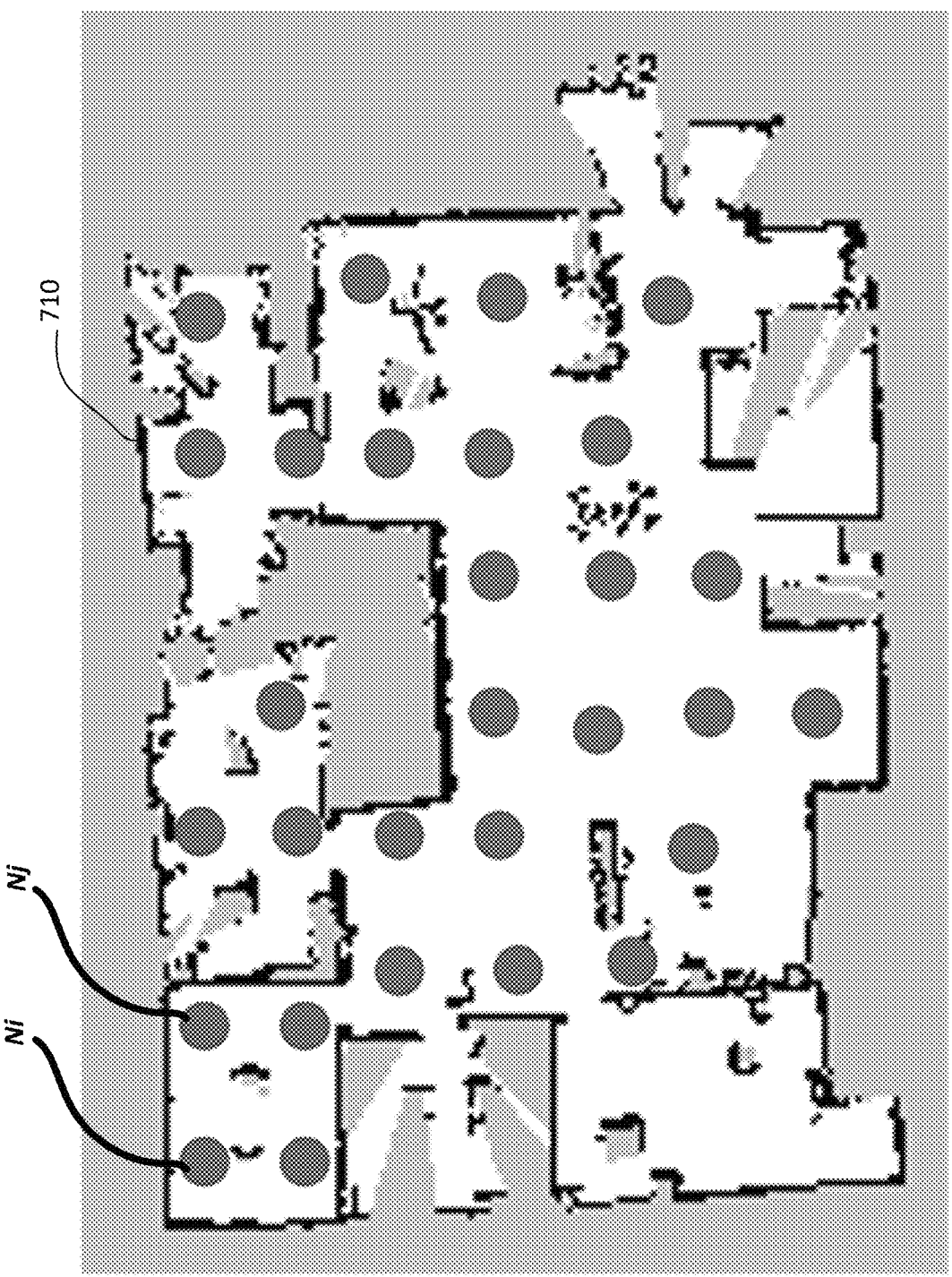
FIG. 7 is a diagram illustrating a SLAM map 700 with node locations.
Figure 8:
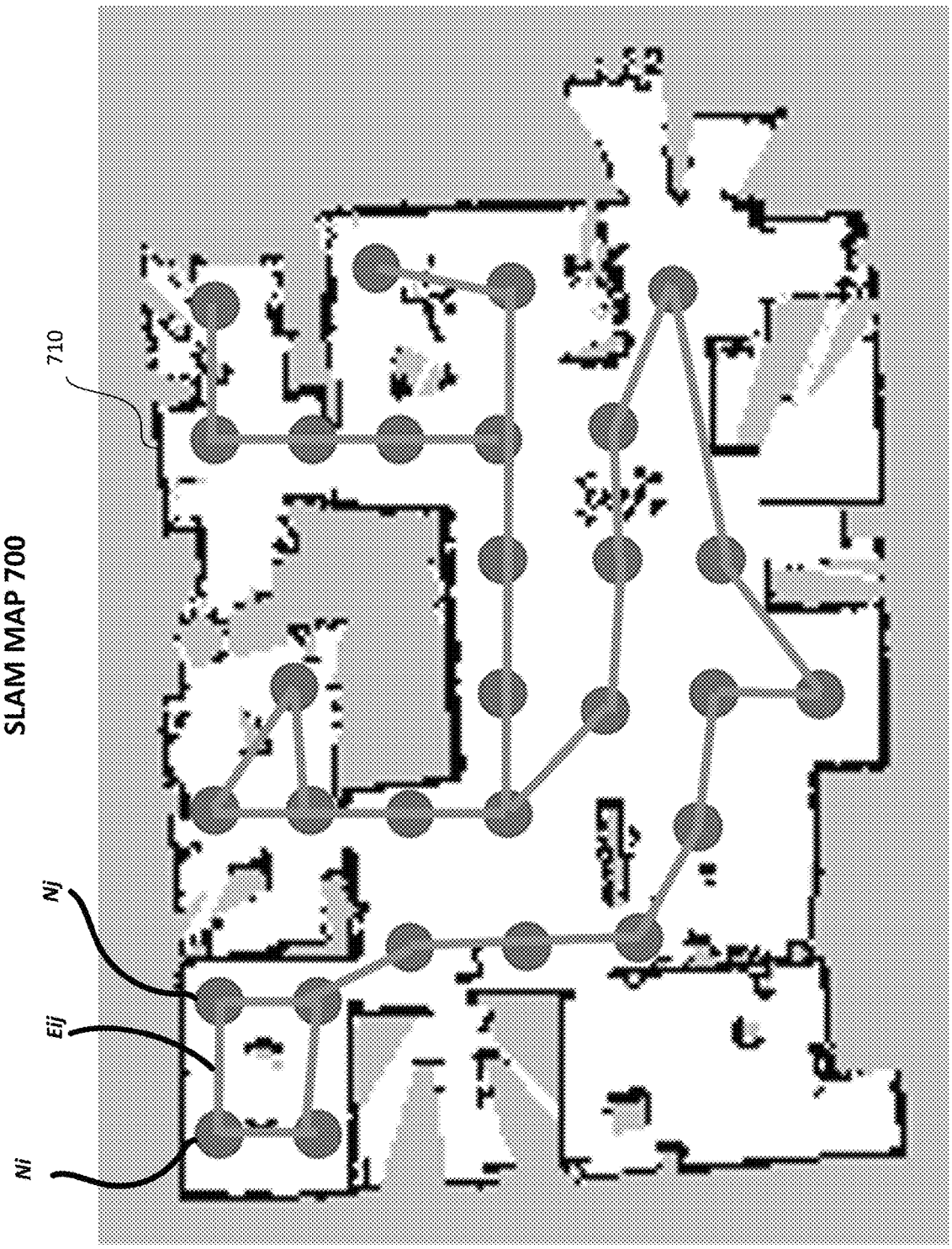
FIG. 8 is a diagram illustrating the SLAM map of FIG. 7 showing an optimal path from one node to another.

FIG. 7 shows a SLAM map 700 of an interior area 710 having a plurality of nodes (illustrated as solid circular objects), each of which are located at particular selected positions with respect to the interior area in the map, and two of the nodes are labeled Ni and Nj. The location of each node comprising the map is fixed by assigning coordinates to the node. A listing of nodes, and the connectivity between them (i.e., edge generated by the function 342), defines a graph structure in which each edge can be assigned a weight that is determined by a dosage of disinfection needed to be applied to the area between two nodes the edge traverses. For example, with reference to FIG. 8 which illustrates the same SLAM map 700 and interior area 710 as shown in FIG. 7, if a dosage of disinfectant is required at nodes $N_i$ and $N_j$, a weighting value of $E_{ij}$ (the dosage amount) will encode a traversal speed for the D-AMR from the node Ni to Nj, as well as well as instructions to control the state of the UVC lights (i.e., one or off) and, according to one embodiment, information used to control UVC lamp orientation.

The PPN module 340 also has graph-search functionality 343 that uses the weighted graph information generated by the graph generation functionality 342 to find an optimal/shortest path from one node to another that allows the D-AMR to visit all nodes within a mapped area and disinfect each feature selected for disinfection. The graph-search functionality can be implemented in any appropriate algorithm such as A* or the Traveling Salesman Problem for example. The information generated by the functions 342 and 343 can be stored in the memory 320 in association with the map information, and as described above, this information can be overlayed on the map information to show a correspondence between features in the map and the weighted graph information.

Figure 5:
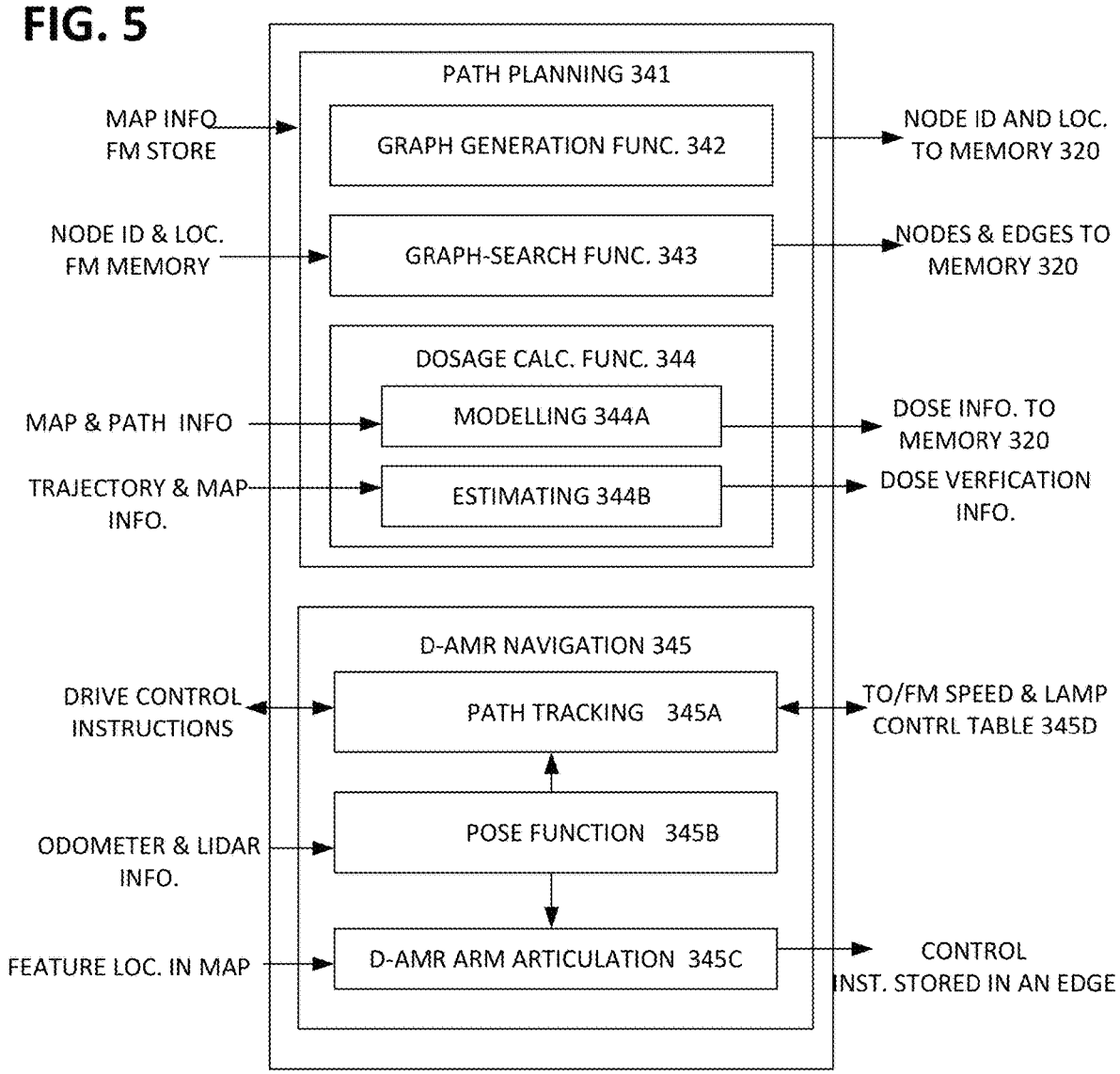
FIG. 5 is block diagram illustrating functional elements comprising a path planning and navigation function 340 associated with either of the D-AMRs 100 and 200.

Continuing to refer to FIG. 5, the PPN module has functionality 344 that uses map information generated by the mapping module 330, path information generated by the path planning module 341, and UVC light configuration and orientation information to calculate a disinfection dosage amount that can be applied to selected features in a mapped area over a period of time that the D-AMR traverses the path.

Regarding the dosage calculation function 344, this functionality is capable of both modeling (344A) and estimating (344B) the UVC dosages respectively can be applied and that are applied to surfaces within the environment. The ability to calculate a dosage applied to each selected feature, allows a certificate of disinfection to be generated which guarantees that the specified dosage requirement at each feature or surface in an area is delivered or not. This disinfection guarantee capability distinguishes the D-AMR described herein from other mobile UVC fixtures, which do not have precise localization and mapping, nor the model of UVC dosage.

Modeling Dosage Applied by the D-AMR-343A.

Continuing to refer to FIG. 5, for a particular configuration of UVC lamps comprising the D-AMR, and using map and path information, it is possible to calculate a model of UVC radiation that can be applied to accurately predict a dosage any selected feature or surface within a particular area can receive. A simple model of UVC intensity follows an inverse-squared distance relationship. This relationship is used to estimate the dosage received from a single UVC lamp within line-of-sight of a point, and informs the disinfection models based on payload configurations. The modelling functionality 344A operates to calculate a predicted disinfection dosage that can be used to assign a weight to an edge in the weighted graph generated by the graph-search function 343.

Dosage Received from a UVC Light Source

The model of UVC dosage assumes a radially-symmetric light source, such as a single UVC lamp. Consider a UVC lamp at location $b^i=(x_b, y_b, z_b, \theta_b)$ in a 3D grid, where $(x_b, y_b, z_b)$ is the position of the D-AMR and $\theta_b$ is the heading of the D-AMR. The dosage, $d^i_\tau$, of UVC light received at a point $p=(x,y,z)$ at a single time step is expressed in Equation 1 as being proportional to the inverse squared distance to that point.

$$d^i_\tau(p, b^i) = \frac{\alpha}{r^2}\Delta t, \quad \text{Equation 1}$$

where $\alpha$ is a constant dependent on the power of the light, $r^2=\|b^i-p\|^2$, and $\Delta t$ is an elapsed time. The units of $\alpha$ are in Watts, the units of distance are in centimeters, and the units of dosage $d^i_\tau(p, b^i)$ are in Watt-seconds per square-centimeter.

Dosage Models Based on Robot Configuration

According to one embodiment, a modular D-AMR payload design can have multiple UVC lighting configurations that deliver a disinfection dosage to the environment in a pattern that is more complex than the $$\frac{\alpha}{r^2}$$

relationship describe above. For a single UVC light source, the unobstructed dosage will be modified by the payload configuration. The dosage, $D^i_\tau(p, b^i)$, delivered in Equation 2 below, as $$D^i_\tau(p,b^i)=f(d^i_\tau(p,b^i)), \quad \text{Equation 2:}$$

where $f(d^i_\tau(p, b^i))$ is a footprint function.

The exact form of the footprint function $f( )$ will depend on occlusions between the payload/UVC light configuration, to any given point. For example, an according to one embodiment, consider a payload configuration with reflectors, we could choose to write the disinfection dosage delivered as a piece-wise function, expressed as in Equation 3 below:

$$D^i_\tau(p, b^i) = \begin{cases} d^i_\tau(p, b^i) & \text{if } \varphi_1 \leq \theta^i \leq \varphi_2 \\ 0 & \text{else} \end{cases} \quad \text{Equation 3}$$

In this example, the disinfection dosage received by a feature from a UVC lamp light from a payload having a reflector is defined by where the point (p) associated with the feature is within the angles $(\varphi_1,\phi p_2)$ from the robot as constrained by the reflector and/or the orientation of the UVC lamp, otherwise, the light will not reach that point.

To construct a dosage model based on a UVC light configuration, a summation of all lights on the payload is considered, their visibility relative to points in the environment is considered, and the orientation of the robot, or the orientation of the lamps, within the environment or the orientation of the UVC lamps is considered. To illustrate how a dosage footprint can be constructed, let $b^i$ refer to the ith lamp of m total lamps on a payload. A dosage received at a single timestep can be re-written as in Equation 4 below:

$$D_\tau(p,b^i, \ldots, b^m)=\Sigma_{i=1}^m D^i_\tau(p,b^i), \quad \text{Equation 4:}$$

where the total dosage delivered from the payload $D_\tau$ is the summation of the dosage delivered by each individual light $D^i_\tau$.

Computing Dosage, D(p,b), Accumulation for a Mobile Robot Over Time

If the D-AMR is stationary, then the dose can be calculated in one step by the total elapsed time. However, as the D-AMR moves, the distance between the D-AMR and the point to be disinfected changes. The computation of the total accumulated dosage at a point as the sum of all dosages at each time step is expressed in Equation 5 below:

$$D(p,b)=\Sigma_{\tau=1}^n D_\tau(p_t,b_t), \quad \text{Equation 5:}$$

wherein, $\tau$ represents a discretized time step, and n is the total number of steps. If our recorded robot trajectory has 100 points, then n=100, and for each unique point in the trajectory, a $D_\tau$ calculation is performed using Equation 4. Note that $\Delta t$ can be computed as the elapsed time between trajectory samples. The expression D(p,b) provides an estimate of the accumulated dosage at a point in the environment over time for a mobile robot moving through the space. Here, $D_\tau(p_t, b_t)$ represents the dosage pattern from the robot for a single time step. The design of $D_\tau(p_t, b_t)$ should follow from the configuration of the UVC lights within the payload, and different payload configurations will have different dosage models.

Verifying Dosage Received in 2D and 3D

Referring now to the estimating function 344B in FIG. 5, during each traverse of a path, the D-AMR collects odometry information, sensor data, and applied dosage information generated using Equation 5. From the trajectory history and map information, the function 344B can estimate a total dosage of UVC radiation that was applied to all surfaces within the environment. For each point in time, there is a corresponding position of the D-AMR within a map, as well as any sensor information (such as camera and lidar information). To accurately calculate and verify the dosage, the D-AMR relies on sensor data to account for occlusions within the area along that path. For instance, since lidar gives distances to walls and objects in the environment, it is a natural proxy for the line-of-sight coverage of the UVC dosages. It is possible to reconstruct a footprint of dosage from the lidar information at each point in time along the path to the points known to be visible to the D-AMR at that point in time. With a 2D lidar device, it is possible to create this map flattened in the z-dimension. Information generated by a 3D lidar device can be used to reconstruct a 3D walk-through of the environment, with the known dosage at every point in the 3D space.

Visualizing Dosage Applied in 2D and 3D

Figure 9:
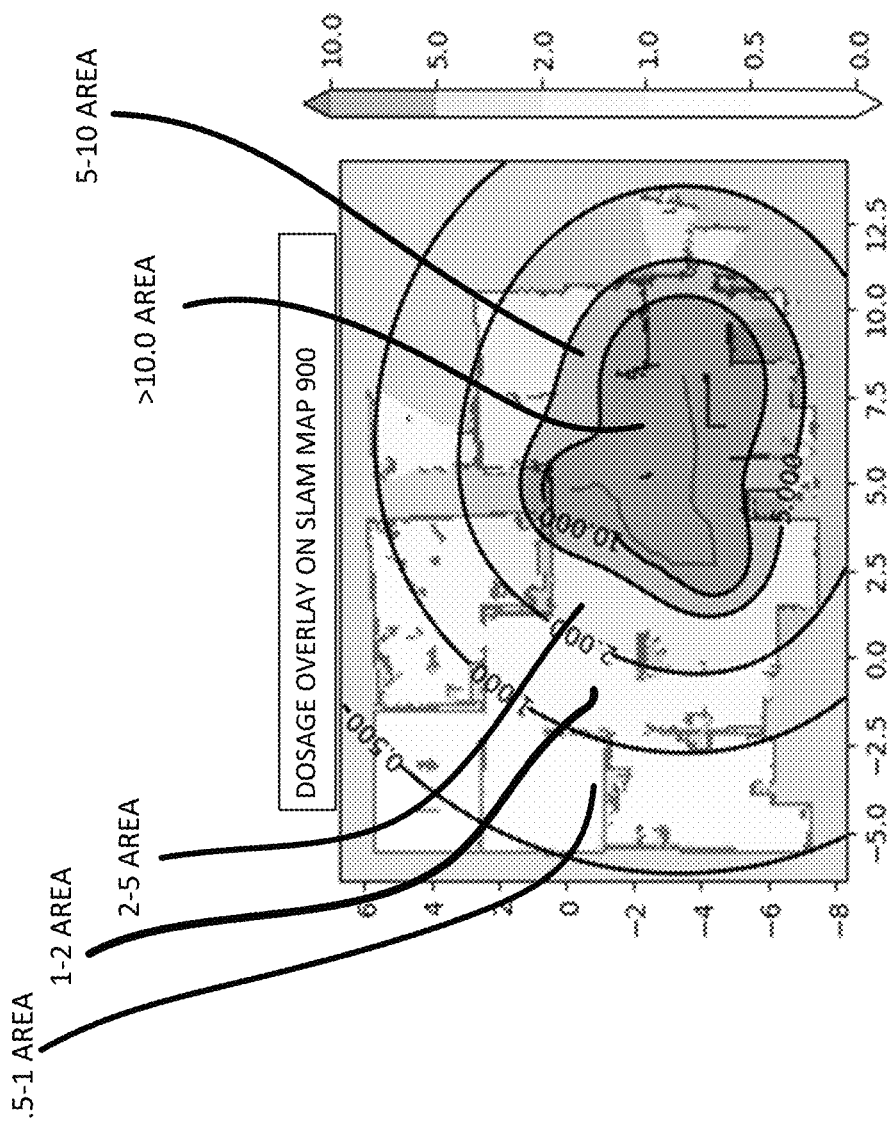
FIG. 9 is a diagram of a disinfection heat map 900.

Subsequent to dosages delivered in an area being verified by the estimating function 344B, a map visualizing the effectiveness of the disinfection process can be generated. Using information generated by the estimating function 344B, a 2D heatmap can be generated having a color gradient that denotes the various dosage thresholds delivered by the robot in time. Color can range from red to blue, with red representing an area in which an adequate or high dosage of disinfectant is applied and blue representing an area in which a low or inadequate dosage of disinfectant is applied. This heatmap can be overlaid onto a building floorplan or a SLAM map to create a dosage report for the end user, where all points in the robot's SLAM map are translated into the coordinates of the end user's map. Such a heatmap 900 is illustrated with reference to FIG. 9. More specifically, since the disinfection dosage applied to each location (i.e., location defined by 2-D or 3-D coordinates (x,y) or (x,y,z) respectively) in a space is known, these locations can be plotted and then overlayed onto a map of the space in a manner that shows a gradient change from one area of greater disinfection to an area of lesser disinfection. This heatmap can be implemented in python or any other appropriate scripting language.

In 3D, lidar or camera information recorded by the D-AMR during a path traverse is sufficient to generate a 3D reconstruction of an area. Within the 3D reconstruction, the surfaces of this model can be colored, with the colormap corresponding to the overall dosage received. An end user would be able to either explore the model in an interactive fashion, or a simulation replaying the D-AMRs trajectory in the modeled environment can be provided to the user.

Referring again to FIG. 5, the D-AMR navigation functionality 345 generally operates to examine information comprising a map to generate navigation instructions that the D-AMR can use to move from one node, or waypoint, to the next node along a path through an area to be disinfected. The navigation function 345 has a path tracking function 345A, pose determination function 345B and D-AMR arm articulation control functionality 345C. The path tracking function 345A can be implemented in any appropriate algorithm that operates to calculate an angular velocity from a current, known location (i.e., a current node location), to a next node location along a path using the information generated by the path planning function 34. In order to operate, the tracking function uses information generated by the pose function 345B, which in turn operates using a current location of the D-AMR (which can be determined using odometer information) and sensor information, such a lidar or other sensor information, to determine the current location and pose (orientation within a mapped space). This pose information can be maintained until used by the tracking function. The odometer information can be received from an odometer device operating in association with a D-AMR drive system (not shown), and this information is generally saved as a distance travelled in feet, for example, from a starting location to the current location of the D-AMR.

Continuing to refer to FIG. 5, the speed at which the D-AMR moves from one node to another can be determined by an amount of disinfection that is needed as the D-AMR traverses a path between the nodes. And this traversal speed corresponds to a disinfection dosage assigned to an edge, as a weight, that corresponds to the path between the two nodes. This weight encodes a particular speed at which the D-AMR moves along the path between the two nodes and it encodes the state of the UVC lamps comprising the D-AMR. The encoded information associated with the speed and lamp control can be contained in a table 345D shown with reference to FIG. 6. The speed and lamp state information comprising the Table 345D is generated by the path planning module 340. As shown in in the table, each of three doses, A, B and C, calculated by the path planning module 340 is associated with a speed (in meters per second) and a lamp state (on or off). Alternatively, the speeds and lamp state information can be generated manually by an expert user based on a dosage requirement and a type of feature to be disinfected in an area. And, according to one embodiment, instructions used to control the orientation of a UVC lamp comprising the D-AMR can also be associated with each edge. In this regard, knowing a starting orientation for each D-AMR arm, the orientation of the D-AMR in the mapped area (from the pose information), and knowing the location of a feature selected for disinfection with respect to the current location of the D-AMR, the functionality 345C can operate to generate arm articulation instructions that can be used to control the arm movement to direct a UVC lamp towards a feature in the area selected for disinfection. An arm can operate to raise or lower a lamp with respect to a floor plane, it can operate to rotate a lamp around a horizontal or vertical axis alter the direction of the UVC radiation emitted from the lamp, and it can operate to extend a lamp away from the D-AMR body towards a feature to be disinfected.

Regarding the functionality 341 that operates to select that location or locations and identities of each of one or more nodes comprising the map, this functionality can be controlled by the D-AMR to run independently to select node locations, or the node locations can be selected under user control. Regardless of whether the position of nodes is selected by the D-AMR or user, the position of each node is selected such they can provide a sufficient dose of disinfection to all features, and surfaces of interest comprising an area. These nodes are not necessarily evenly spaced, but instead spaced at a distance such that if a robot visits a node, it will provide sufficient dosage to the environment surrounding that node. For example, if a room contains four nodes, by visiting all four nodes, the robot provides sufficient dosage to the entire room. Nodes are also placed as navigation waypoints between regions of disinfection, such as navigating down a corridor to an area.

What is claimed is:

1. A method of disinfecting an interior space, comprising:
   generating a map of the interior space using information collected by a sensor system comprising an autonomous, mobile, robotic (AMR) device, and determining from the collected sensor information an identity and location of one or more areas for disinfection;
   using the map of the interior space, and the location of the one or more areas identified for disinfection, to determine a path for the AMR device to follow through the interior space in order to disinfect each of the one or more areas identified for disinfection, wherein the path comprises a plurality of nodes;

calculating a dosage of disinfectant to be applied by the AMR device to each of the one or more areas identified for disinfection along the path; and controlling the AMR device to traverse the path while it applies the calculated dosage of disinfectant to each of the one or more areas, wherein a traversal speed corresponds to the disinfection dosage assigned to an edge, as a weight, that corresponds to the path between two adjacent nodes is determined, and wherein the weight comprises at least a speed of the AMR device and the dosage of disinfectant.

2. The method of claim 1, wherein a neural network is trained to identify the one or more areas for disinfection.

3. The method of claim 1, wherein a location for at least one waypoint along the path is selected so that all of the areas identified for disinfection receive a calculated dose of infection.

4. The method of claim 3, wherein the location of the at least one waypoint is selected by either an AMR device user or by the AMR device.

5. The method of claim 3, further comprising the AMR device being controlled to traverse the path from a starting location to the at least one waypoint while it applies a calculated dosage of disinfectant.

6. The method of claim 3, wherein the at least one waypoint corresponds to a node from the plurality of nodes in a graph structure generated by a path planning function comprising the AMR device.

7. The method of claim 6, wherein the graph structure is comprised of the plurality of nodes, and a path between a first node and a second node is indicative of the existence of an edge.

8. The method of claim 7, wherein the edge is assigned a weight that is associated with a particular dose of disinfectant to be applied by the AMR device as it traverses the edge.

9. The method of claim 1, wherein the information collected by the sensor system is used to generate a two or a three-dimensional map.

10. The method of claim 1, wherein the rate of speed at which the AMR device traverses the edge corresponds to an amount of disinfectant dosage that is calculated to be applied to an area that is proximate to the edge.

11. The method of claim 1, wherein the areas for disinfection are features or surfaces comprising the interior space.

12. The method of claim 1, wherein the dosage of disinfectant is calculated using map information, optimal path information and AMR device UVC light configuration information.

13. The method of claim 12, wherein the UVC light configuration information is comprised of any one or more of a number, type, intensity and orientation of one or more UVC light sources attached to the AMR device.

14. A method of disinfecting an interior space, comprising:

generating a two or three-dimensional map of the interior space using information collected by a sensor system comprising an autonomous, mobile, robotic (AMR) device, and determining from the collected sensor information an identity and location of one or more areas for disinfection;

using the map of the interior space, and the location of the one or more areas identified for disinfection, to determine an optimal path for the AMR device to follow through the interior space in order to disinfect each of the one or more areas identified for disinfection, wherein the optimal path comprises a plurality of nodes;

calculating a dosage of disinfectant to be applied by the AMR device to each of the one or more areas identified for disinfection along the optimal path; and controlling the AMR device to traverse the optimal path while it applies the calculated dosage of disinfectant to each of the one or more areas, wherein a traversal speed corresponds to the disinfection dosage assigned to an edge, as a weight, that corresponds to the path between two adjacent nodes is determined, and wherein the weight comprises at least a speed of the AMR device and the dosage of disinfectant.

15. The method of claim 14, wherein a location for at least one waypoint along the path is selected so that all of the areas identified for disinfection receive a calculated dose of disinfectant.

16. The method of claim 15, further comprising the AMR device being controlled to traverse the path from a starting location to the at least one waypoint while it applies a calculated dosage of disinfectant.

17. The method of claim 15, wherein the at least one waypoint corresponds to a node from the plurality of nodes in a graph structure generated by a path planning function comprising the AMR device.

18. The method of claim 17, wherein the graph structure is comprised of the plurality of nodes, and a path between a first node and a second node is indicative of the existence of an edge.

* * * * *